United States Patent
Shickle (10) Patent No.: US 7,832,807 B2
(45) Date of Patent: Nov. 16, 2010

(54) SECUREMENT DEVICE

(76) Inventor: Nina Shickle, 7051 Encino Ave., Lake Balboa, CA (US) 91406

( * ) Notice: Subject to any disclaimer, the term of this patent is extended or adjusted under 35 U.S.C. 154(b) by 162 days.

(21) Appl. No.: 12/214,571

(22) Filed: Jun. 19, 2008

(65) Prior Publication Data

US 2009/0315385 A1    Dec. 24, 2009

(51) Int. Cl.
*B60R 22/00* (2006.01)
(52) U.S. Cl. .................................. 297/466; 297/485
(58) Field of Classification Search ............. 297/393, 297/397, 464, 466, 473, 485
See application file for complete search history.

(56) References Cited

U.S. PATENT DOCUMENTS

| | | | | |
|---|---|---|---|---|
| 579,818 A | * | 3/1897 | Cooley | 297/468 |
| 2,288,692 A | * | 7/1942 | Fearson | 297/473 |
| 3,385,633 A | * | 5/1968 | Aizley | 297/473 |
| 4,192,546 A | * | 3/1980 | Smith | 297/466 |
| 4,205,670 A | * | 6/1980 | Owens | 297/485 |
| 4,707,031 A | * | 11/1987 | Meistrell | 297/393 |
| 4,898,185 A | * | 2/1990 | Fuller | 297/485 |
| 5,215,354 A | * | 6/1993 | Grene | 297/485 |
| 5,345,633 A | * | 9/1994 | Harnish | 297/397 |
| 6,607,245 B1 | * | 8/2003 | Scher | 297/393 |

* cited by examiner

*Primary Examiner*—Peter R. Brown (57) ABSTRACT

A restraining strap assembly for restraining a person in a wheelchair which is made up of two cooperating securement strap assemblies, namely a chair securement strap assembly that is secured to the wheelchair seat and a person securement strap assembly that can be removably interconnected with the chair securement strap assembly as is used to prevent inadvertent separation of the person's legs. The chair securement strap assembly includes a pair of elongated, spaced apart strap segments that circumscribe and are connected to the seat of the wheelchair. The person securement strap assembly which is releasably connected to the chair securement strap assembly can be easily positioned by the handicapped person about his or her legs in a manner to keep the legs together.

10 Claims, 6 Drawing Sheets

SECUREMENT DEVICE

BACKGROUND OF THE INVENTION

1. Field of the Invention

The present invention relates generally to securement devices. More particularly, the invention concerns a securement device for securing a disabled person within a wheelchair.

2. Discussion of the Prior Art

A person who is wheelchair-bound and has no physical control over, or capability of, keeping their legs closed, often has difficulty maintaining their feet securely in position on the foot plates of the wheelchair. Additionally, a wheelchair bound person may suffer leg spasms that cause the feet to involuntarily fall from the foot plates thereby rendering them virtually helpless and forcing them to wait for someone to come to their assistance.

This problem is particularly serious for individuals who have limited, or no feeling in the lower part of their legs. In such situations it is possible for the person to involuntarily run over their own feet and possibly fall from the wheelchair, causing serious injury.

While various types of securement straps have been suggested in the past, individuals with limited dexterity have great difficulty in manipulating the prior art securement straps, and require assistance from others when it is necessary to leave the wheelchair for hygienic or other purposes. Accordingly, there has long existed a pressing need to develop a securement strap system that enables wheelchair-bound persons to easily manipulate the securement straps at their own convenience for hygienic purposes and thereby eliminate the humiliation of constantly asking for assistance.

To avoid the embarrassment caused by involuntary leg separation, wheelchair-bound persons have at times resorted to the use of a conventional belt to keep their legs together. Such an approach is generally unsatisfactory, particularly for persons having limited dexterity. For example, if the disabled person accidentally drops the belt while attempting to connect, or disconnect the belt, assistance must be sought to retrieve the belt. Similarly, if the position of the belt shifts so that it cannot easily be manipulated, once again assistance must be sought. These types of situations are highly undesirable because the wheelchair-bound person who is troubled with involuntary leg separation and must continually ask for assistance, often becomes embarrassed and demoralized and can at times becomes frustrated and belligerent.

SUMMARY OF THE INVENTION

By way of summary, one form of the restraining strap assembly of the present invention for restraining a person in a wheel chair comprises two cooperating securement strap assemblies, namely a chair securement strap assembly and a person securement strap assembly that can be removably interconnected with the chair securement strap assembly. In a preferred form of the invention the chair securement strap assembly comprises a pair of elongated, spaced apart strap segments that circumscribe the seat of the wheelchair or like device. Each of the strap segments has a first end, a second end and an intermediate portion. Connectors are provided at each end of each of the strap segments to enable the first and second ends of the strap segments to be releasably interconnected. A person securement connector strap assembly of novel design invention is connected to the intermediate portions of the first and second strap segments. This connector strap assembly permits the person securement strap assembly to be releasably interconnected with the chair securement strap assembly.

With the forgoing in mind, it is an object of the present invention to provide a novel restraining strap assembly for restraining a handicapped person within a chair, within a manually operated wheelchair, or within an electrically operated wheelchair.

Another object of the invention is to provide a restraining strap assembly that can be quickly and easily securely interconnected with the chair or wheelchair and, once interconnected, can be easily used by the handicapped person to prevent inadvertent leg separation.

Another object of the invention is to provide a restraining strap assembly of the aforementioned character that secures the handicapped person within the wheelchair in a manner such that the person's feet will not inadvertently fall from the supporting plates of the wheelchair.

Another object of the invention is to provide a restraining strap assembly of the character described in the preceding paragraph that secures the handicapped person within the wheelchair in a manner to prevent a person from accidentally falling from the wheelchair.

Another object of the invention is to provide a restraining strap assembly for securing a handicapped person within a wheelchair that is of simple construction and one in which the person securement strap component can be easily manipulated by persons with limited dexterity.

Another object of the invention is to provide a restraining strap assembly as described in the preceding paragraphs that is of durable construction and is highly reliable in use.

The foregoing, as well as other objects of the invention can be achieved by the restraining strap assembly illustrated in the drawings and described in the paragraphs which follow,

DESCRIPTION OF THE INVENTION

Figure 1:
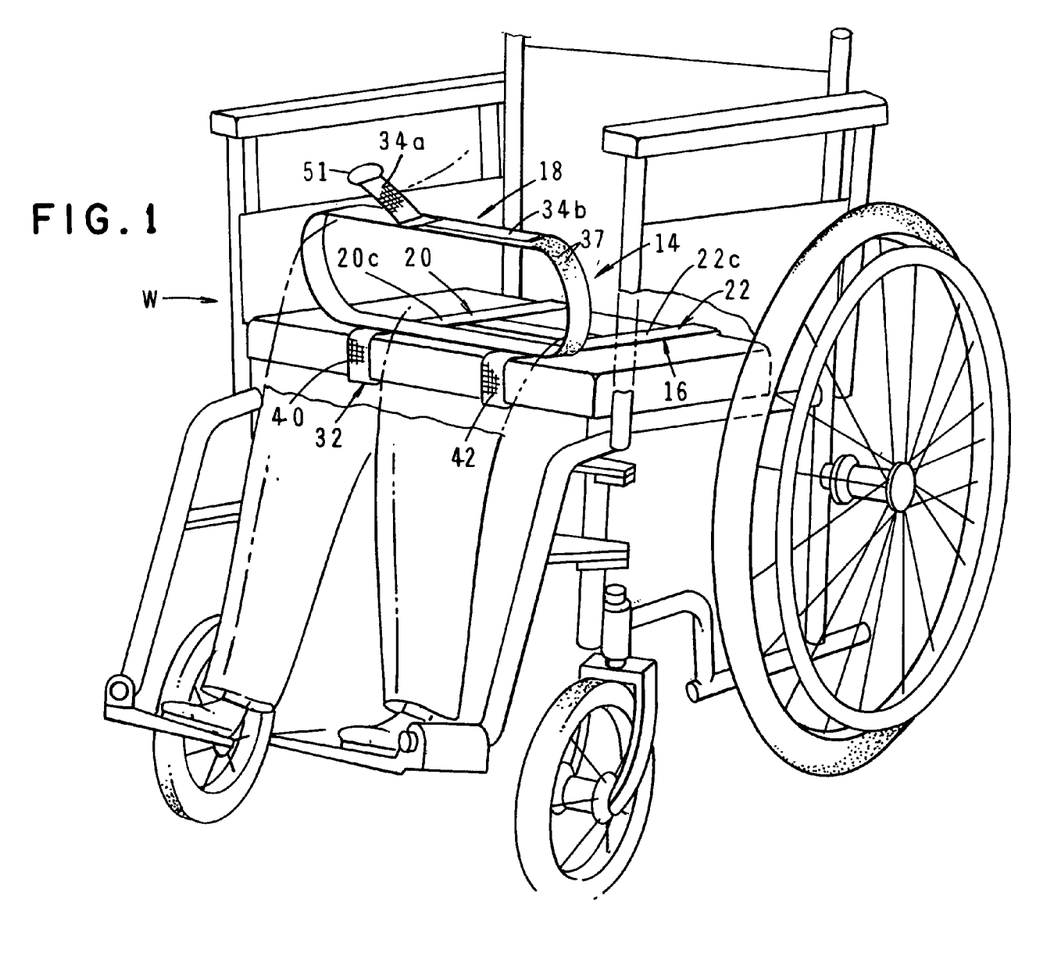
FIG. 1 is a generally perspective view illustrating the use of the securement strap apparatus by an individual sitting in a wheelchair.
Figure 2A:
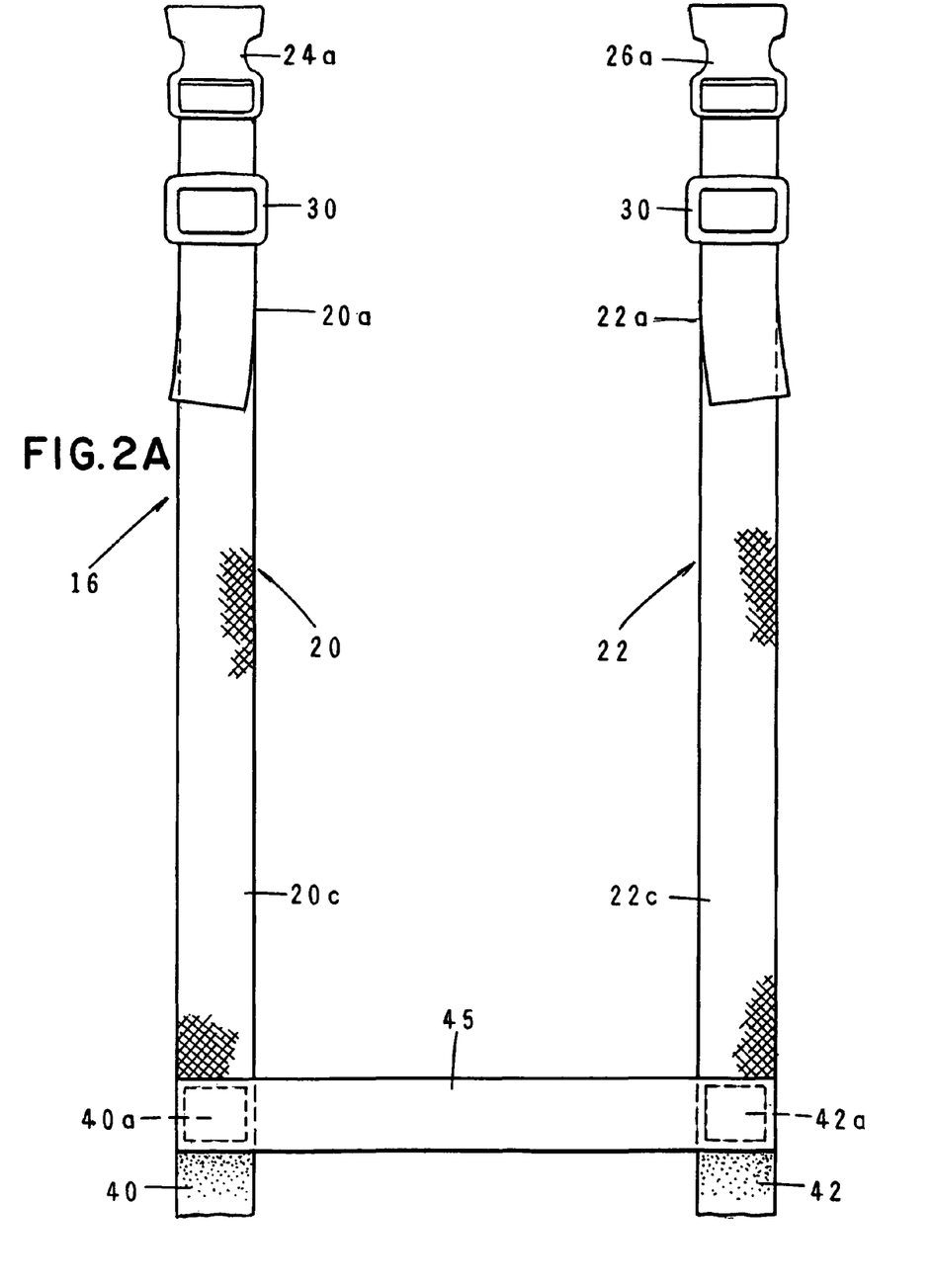
FIGS. 2A and 2B, when considered together, comprise a top plan view of the securement strap apparatus of the invention.
Figure 2B:
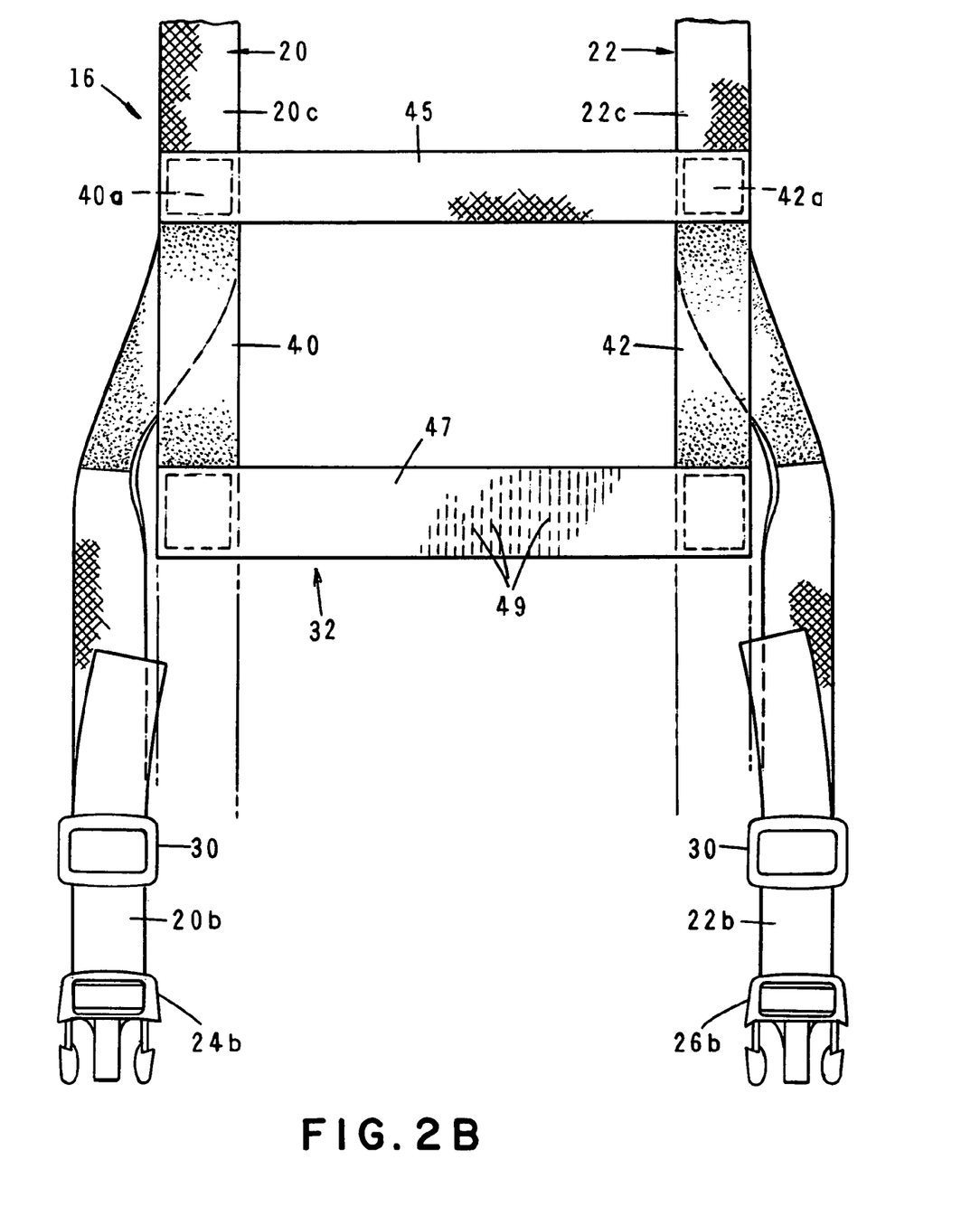

Referring to the drawings and particularly to FIGS. 1, 2A and 2B, one form of the restraining strap assembly of the invention for restraining a person in a wheelchair is there shown and generally identified by the numeral 14. Restraining strap assembly 14 here comprises two cooperating securement assemblies, namely a chair securement strap assembly generally designated as 16 and a person securement strap assembly generally designated as 18.

Considering first the chair securement strap assembly 16, this novel assembly comprises a pair of elongated, spaced apart strap segments 20 and 22. Segments 20 and 22 can be constructed from various materials, but are preferably constructed a from a heavyweight polypropylene braided webbing material. Strap segment 20 has a first end portion 20a (FIG. 2A), a second end portion 20b (FIG. 2B) and an intermediate portion 20c (FIG. 2B). Similarly, strap segment 22 has a first end portion 22a (FIG. 2A), a second end portion 22b (FIG. 2B), and an intermediate portion 22c (FIG. 2B). Connected to first end portion 20a of first strap segment 20 is a first connector, shown here as the female part 24a of a conventional, readily commercially available double-sided snapping buckle lock, the male part 24b of which is connected to the second end portion 20b of first strap segment 20 (FIG. 2B). Parts 24a and 24b of the first connector function in a conventional manner to interconnect the first end portion 20a of the first strap segment with the second end portion 20b of the first strap segment when the first strap segment is positioned over the wheelchair seat in the manner shown in FIG. 1.

Connected to first end portion 22a of second strap segment 22 is a second connector, shown here as the female part 26a of a conventional, readily commercially available double-sided snapping buckle lock, the male part 26b of which is connected to the second end portion 22b of first strap segment 22 (FIG. 2B). Parts 26a and 26b of the second connector function in a conventional manner to interconnect the first end portion 22a of the first strap segment with the second end portion 22b of the second strap segment when the second strap segment is positioned over the wheelchair seat.

As illustrated in FIGS. 2A and 2B, conventional adjustments buckles 30 are provided proximate each end portion of each of the first and second strap segments so as to permit adjustment in a conventional manner of the overall length of the first and second strap segment to accommodate wheelchair seats of various sizes and configuration.

Figure 5:
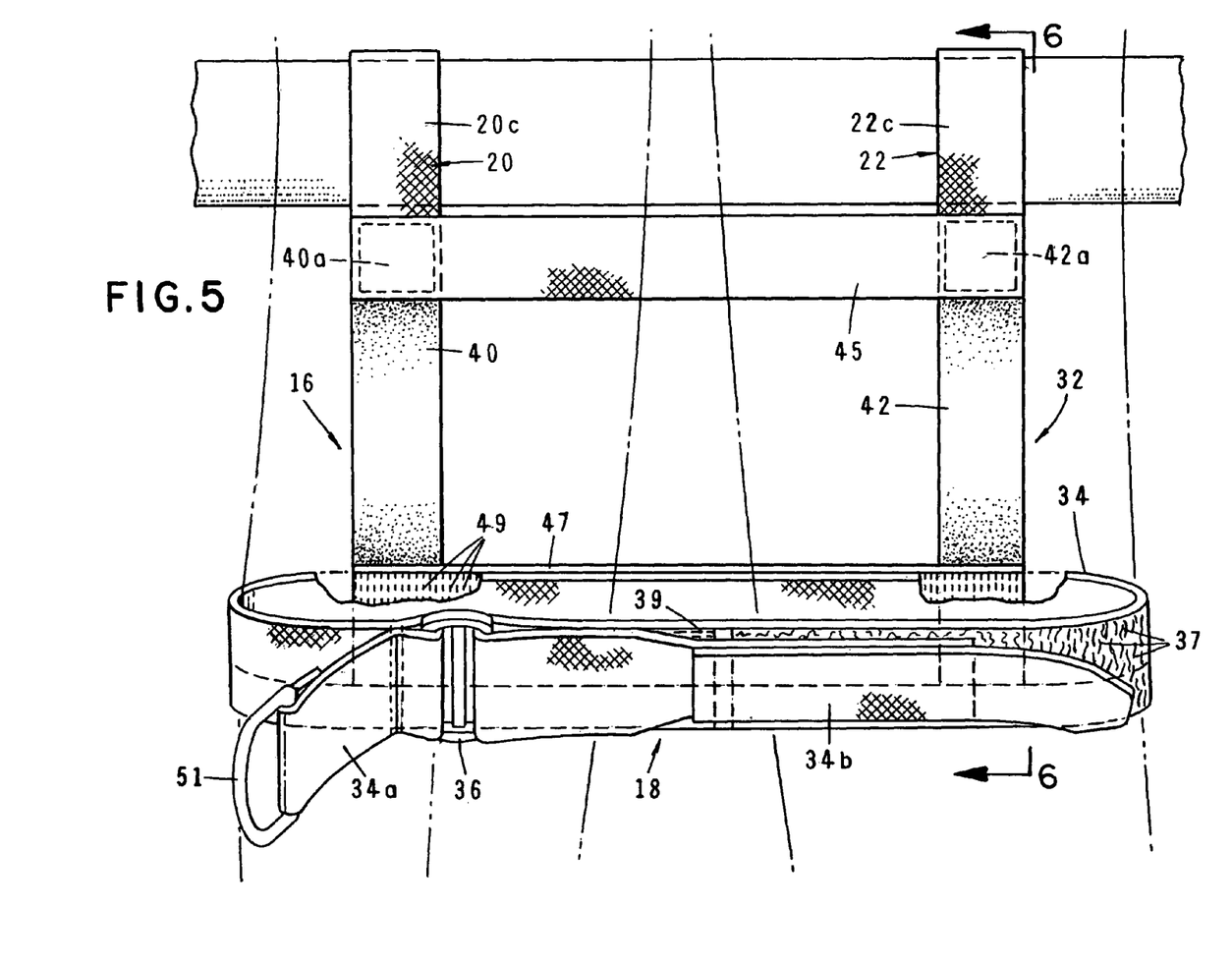
FIG. 5 is a generally perspective front view showing the leg securement strap interconnected with the portion of the apparatus that is secured to the wheelchair.
Figure 6:
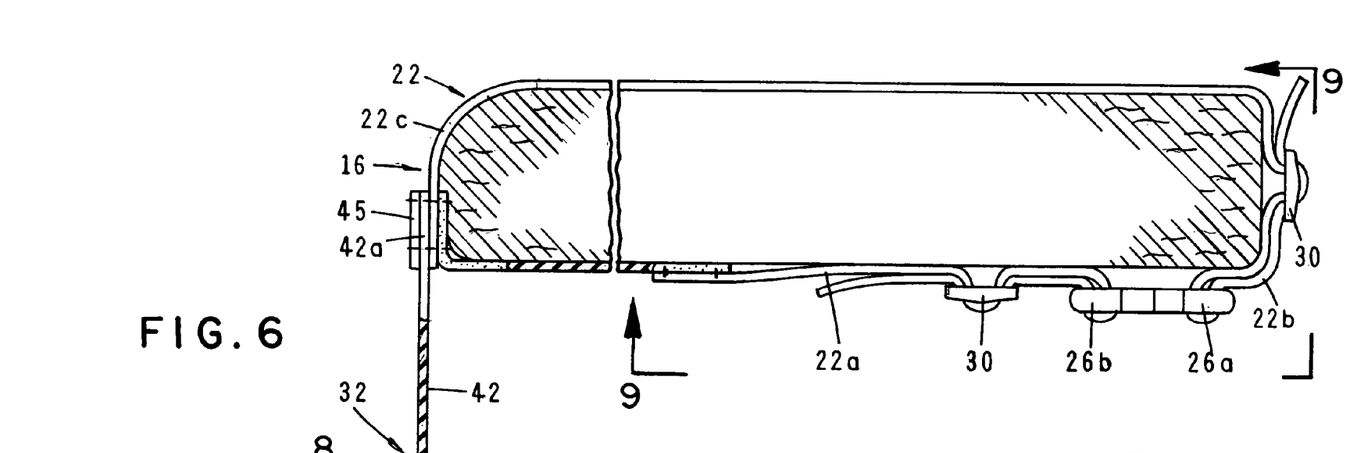
FIG. 6 is a side elevational view of the securement strap apparatus of the invention showing the wheelchair securement strap portion of the apparatus affixed to the seat of the wheelchair and showing the leg securement portion of the apparatus secured to the wheelchair securement strap portion.

Forming an important aspect of the chair securement strap assembly 16 of the invention is a connector strap assembly that is generally designated in FIGS. 2B, 5 and 6 by the numeral 32. Connector strap assembly 32 is connected to the intermediate portions 20c and 22c of the first and second strap segments 20 and 22 in the manner best seen in FIG. 2B. The details of construction and operation of this important strap assembly will presently be discussed.

As best seen in FIGS. 2B and 6 of the drawings, the previously mentioned person securement strap assembly 18 of the invention is releasably connected to the lower portion of the connector strap assembly 32.

Figure 3:
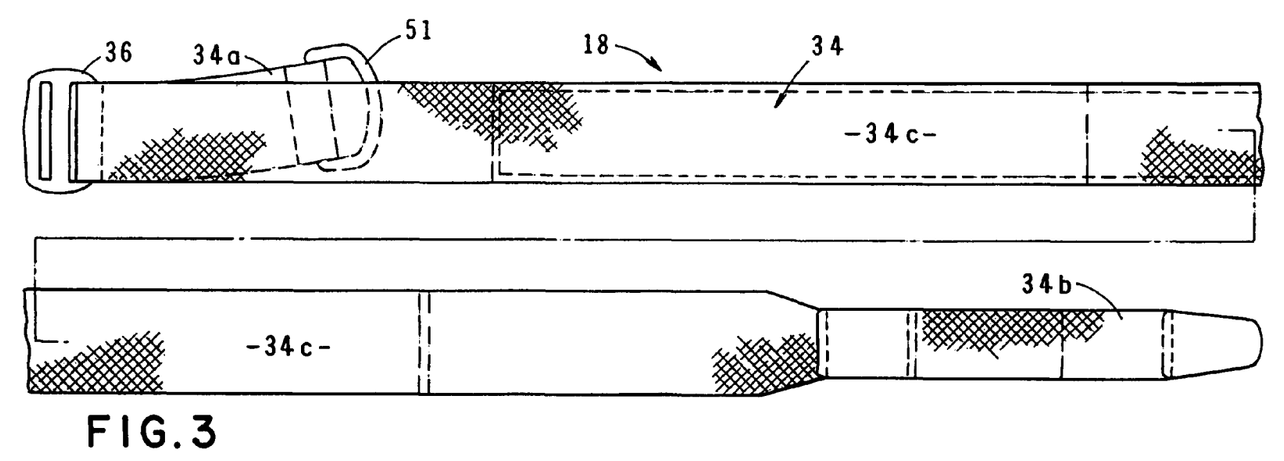
FIG. 3 is a top plan view of one form of the leg securement strap portion of the apparatus of the invention.
Figure 4:
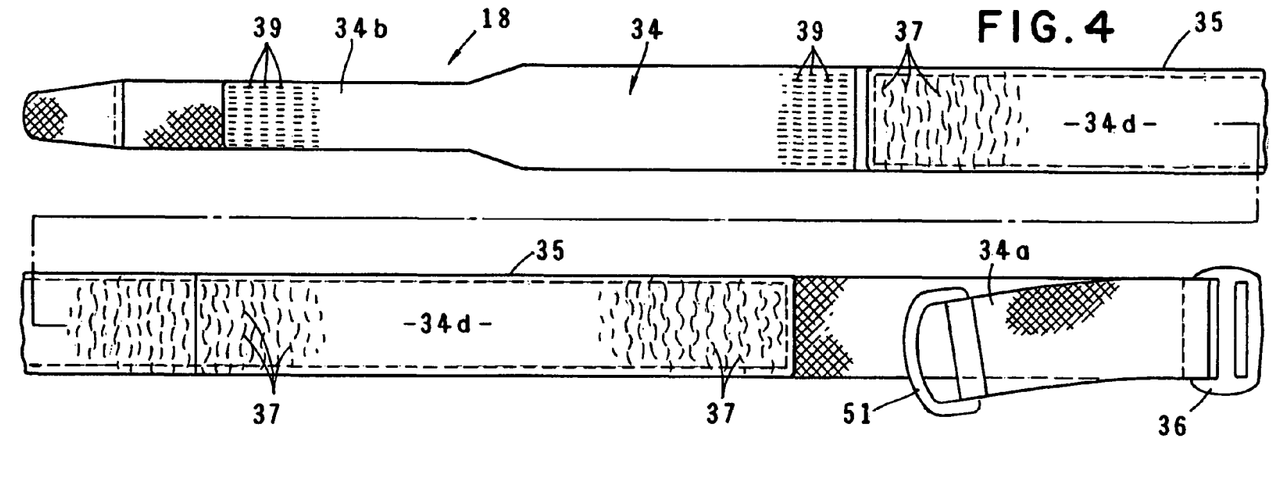
FIG. 4 is a top plan view similar to FIG. 3 but showing the opposite side of the leg securement strap portion.

Person securement strap assembly 18 here comprises a person securement strap 34 having first and second end portions 34a and 34b and first and second sides 34c and 34d respectively (FIGS. 3 and 4). Securement strap assembly 18 can be constructed from various materials, but at least the central portion thereof is preferably constructed from a heavyweight polypropylene braided webbing material. For a reason presently to be described, the central portion 35 of second side 34d is provided with a multiplicity of small loops 37 of the character found in connector materials sold under the name and style "VELCRO". Similarly, for a reason presently to be described, second side 34d of end portion 34b of the person securement strap is provided with a multiplicity of small hooks 39 of the character found in "VELCRO" type connector materials. Connected to first end 34a of the person securement strap is a connector 36, shown here as a conventional buckle type connector, that functions, in a manner presently to be described, to releasably interconnect the first end portion 34a of the person securement strap with the second end portion 34b thereof.

Considering once again the connector strap assembly 32 of the chair securement strap assembly, as shown in FIG. 2B of the drawings this important assembly comprises a first extender segment 40 and a second extender segment 42, both of which are made from a readily commercially available elastic material. As indicated in FIG. 2B, the first end 40a of first extender segment 40 is connected to the intermediate portion 20c of strap segment 20 while second 42a of extender segment 42 is connected to the intermediate portion 22c of strap segment 22. Overlaying the first ends of extender segments 40 and 42 and connected thereto is a first transverse segment 45 that spans the pair of spaced apart strap segments 20 and 22.

Also forming a part of connector strap assembly 32 is a second transverse segment 47 that is connected to and spans the first and second extender segments 40 and 42 in the manner shown in FIG. 2B. Transverse segment 47 is provided with a multiplicity of first connector elements shown here as a multiplicity of small hooks 49 of the character found in connector materials sold under the name and style "VELCRO".

Figures 7, 8, 9:
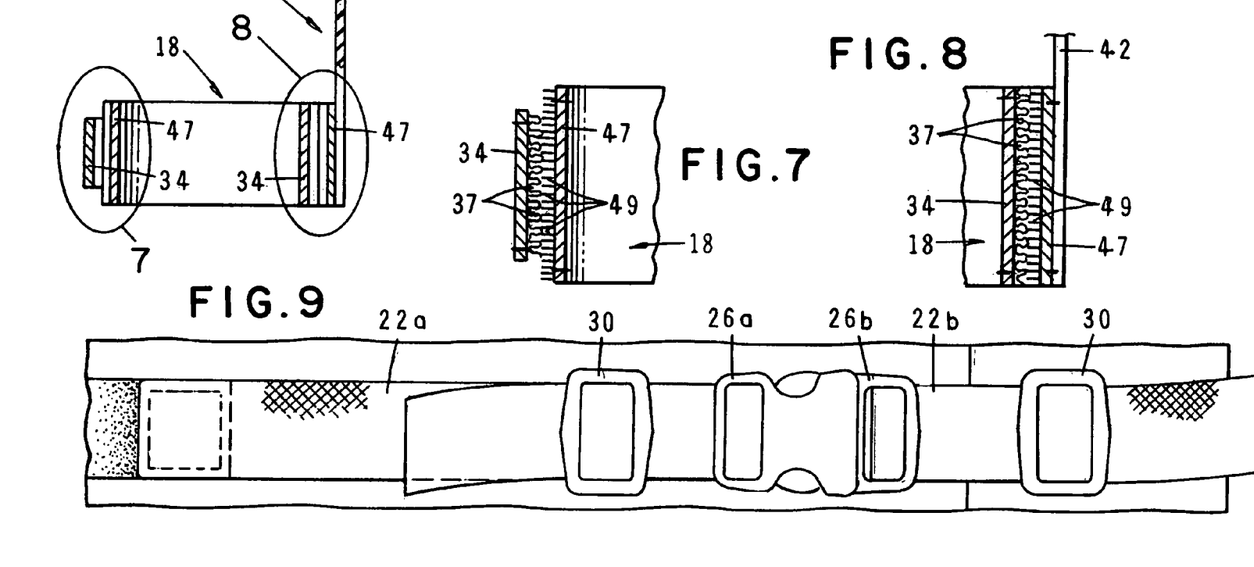
FIG. 7 is a greatly enlarged view of the area designated in FIG. 6 as "7".
FIG. 8 is an enlarged view of the area designated in FIG. 6 as "8".
FIG. 9 is an enlarged view taken along lines 9-9 of FIG. 6.

Referring particularly to FIGS. 1 and 6 of the drawings, in using the securement apparatus of the invention, the securement straps 20 and 22 are laid over the seat of the chair, in this case the wheelchair W, so that the intermediate portion of the straps 20c and 22c are located proximate the front edge of the seat (see FIG. 6). Next, using the conventional adjustment buckles 30, the length of the straps is adjusted so that the end portion 20a and 22b of the straps are located proximate the rear of the seat in the manner shown in FIG. 6. The first portions 20a and 22a of the straps are then extended beneath the seat so that the male connectors 24a and 26a can be interconnected with the female connectors 24b and 26b, respectively, to join the straps in a secure position about the wheelchair's seat in the manner shown in FIG. 1 of the drawings. With the securement straps 20 and 22 properly positioned around the wheelchair seat, the connector assembly 32 will depend downwardly from the front of the seat in the manner shown in FIG. 6 of the drawings. With the connector assembly 32 in this position, the person securement strap 18 can be affixed to the lower transverse member 47 by interconnecting the hook-like elements 49 of member 47 with the loop-like elements 37 of the person securement strap 18 in the manner indicated in FIG. 7 of the drawings.

An important feature of the invention resides in the fact that by simply inverting the securement strap 18 and turning it end for end it can be affixed to the connector assembly so that the strap can be easily operated by either a right-handed or a left-handed person. In either case, as indicated in FIG. 5, once the end 34b of the strap is fed through the connector buckle 36, the forward portion 34b of the strap, which as shown in FIG. 4, is provided with a multiplicity of small hooks, can be releasably interconnected with the intermediate portion of the strap that is provided with a multiplicity of small loops. In order to assist in feeding end 34b of the strap through the connector buckle and in pulling the strap tight about the legs in the manner shown in FIG. 5, a pull ring 51 is provided (See FIGS. 1 and 5).

Because of the construction of the connector harness and the elastomeric members 40 and 42, it can be appreciated that the strap assembly 18 can be affixed about the user's legs at various locations from the knee to the thigh at whatever location is most comfortable.

Once the strap is affixed to the connector harness, there is no danger that it will be accidentally dropped thereby requiring the assistance of a third person. Further, because of the unique design of the person connector strap, it is easy to manipulate and secure about the legs in the manner shown in FIG. 5 of the drawings without the assistance of a third party. Similarly, it is easy for the person to disconnect the person securement harness without the necessity of seeking aid from a third party.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A restraining strap assembly for restraining a person in a chair comprising:
   (a) a chair securement strap assembly comprising:
      (i) first and second elongated, spaced apart strap segments, each of said first and second strap segments having a first end, a second end and an intermediate portion;
      (ii) a first connector connected to said first end of said first strap segment for connecting said first end of said first strap segment to said second end of said first strap segment;
      (iii) a second connector connected to said first end of said second strap segment for connecting said first end of said second strap segment to said second end of said second strap segment; and
      (iv) a connector strap assembly connected to said intermediate portions of said first and second strap segments, said connector strap assembly comprising:
         a. a first transverse segment connected to and spanning said pair of elongated, spaced apart strap segments, said first transverse segment having first and second ends;
         b. a first extender segment connected to said first end of said first transverse segment for extending said second extender segment;
         c. a second extender segment connected to said second end of said first transverse segment for extending said second extender segment; and
         d. a second transverse segment connected to and spanning said first and second extender segments; and
   (b) a person securement strap assembly releasably connected to said second transverse segment of said connector strap assembly of said chair securement strap assembly, said person securement strap assembly comprising a securement strap having first and second ends and a connector connected to said first end of said person securement strap for releasably connecting said first end of said person securement strap to said second end thereof.

2. The restraining strap assembly as defined in claim 1 in which said second transverse segment connector strap segment of said restraining strap assembly is provided with a multiplicity of small hooks and in which a portion of said person securement strap assembly is provided with a multiplicity of small loops.

3. The restraining strap assembly as defined in claim 2 in which said first and second extender segments are constructed of an elastic material.

4. A restraining strap assembly for restraining a person in a chair comprising:
   (a) a chair securement strap assembly comprising:
      (i) first and second elongated, spaced apart strap segments, each strap segment having a first end, a second end and an intermediate portion;
      (ii) a first connector connected to said first end of said first strap segment for connecting said first end of said first strap segment to said second end of said first strap segment;
      (iii) a second connector connected to said first end of said second strap segment for connecting said first end of said second strap segment to said second end of said second strap segment; and
      (iv) a connector strap assembly connected to said intermediate portions of said first and second strap segments, said connector strap assembly comprising:
         a. a first transverse segment connected to and spanning said pair of elongated, spaced apart strap segments, said first transverse segment having first and second ends;
         b. a first extender segment connected to said first end of said first transverse segment for extending said first connector segment;
         c. a second extender segment connected to said second end of said first transverse segment for extending said second connector segment; and
         d. a second transverse segment connected to and spanning said first and second extender segments, said second transverse segment being provided with a multiplicity of small hooks; and
   (b) a person securement strap assembly releasably connected to said second transverse segment of said connector strap assembly of said chair securement strap assembly, said person securement strap assembly comprising a securement strap having first and second ends and a connector connected to said first end of said person securement strap for releasably connecting said first end of said person securement strap to said second end thereof.

5. The restraining strap assembly as defined in claim 4 in which said securement strap of said person securement strap assembly has first and second sides and in which each of said first and second sides is provided with a multiplicity of small loops.

6. The restraining strap assembly as defined in claim 5 in which said first and second extender segments are constructed of an elastic material.

7. A restraining strap assembly for restraining a person in a chair comprising:
   (a) a chair securement strap assembly comprising:
      (i) a pair of elongated, spaced apart first and second strap segments, each said first and second strap segment having a first end, a second end and an intermediate portion;
      (ii) a first connector connected to said first end of said first strap segment for connecting said first end of said first strap segment to said second end of said first strap segment;
      (iii) a second connector connected to said first end of said second strap segment for connecting said first end of said second strap segment to said second end of said second strap segment; and (iv) a connector strap assembly connected to said intermediate portions of said first and second strap segments, said connector strap assembly comprising:
  a. a first transverse segment connected to and spanning said pair of elongated, spaced apart strap segments, said first transverse segment having first and second ends;
  b. a first extender segment connected to said first end of said first transverse segment for extending said first extender segment;
  c. a second extender segment connected to said second end of said first transverse segment for extending said second extender segment; and
  d. a second transverse segment connected to and spanning said first and second extender segments; and
(b) a person securement strap assembly connected to said connector strap assembly of said chair securement strap assembly, said person securement strap assembly comprising a securement strap having first and second ends and a connector connected to said first end of said person securement strap for releasably connecting said first end of said person securement strap to said second end thereof.

8. The restraining strap assembly as defined in claim 7 in which said second transverse segment connector strap segment of said restraining strap assembly is provided with a multiplicity of first connector elements and in which a portion of said person securement strap assembly is provided with a multiplicity of second connector elements releasably interconnectable with said multiplicity of first connector elements.

9. The restraining strap assembly as defined in claim 8 in which said multiplicity of first connector elements comprise a multiplicity of small loops and in which said multiplicity of second connector elements comprise a multiplicity of small hooks.

10. The restraining strap assembly as defined in claim 8 in which said first and second extender segments are constructed of an elastic material.

* * * * *